(12) United States Patent
Fujii

(10) Patent No.: US 7,351,209 B2
(45) Date of Patent: Apr. 1, 2008

(54) APPARATUS FOR INSPECTING ALLERGIC REACTION

(76) Inventor: Hitoshi Fujii, 26-8, Hinosato 2-chome, Munakata-shi, Fukuoka 811-3425 (JP)

(*) Notice: Subject to any disclaimer, the term of this patent is extended or adjusted under 35 U.S.C. 154(b) by 635 days.

(21) Appl. No.: 10/654,325

(22) Filed: Sep. 2, 2003

(65) Prior Publication Data
US 2004/0176701 A1  Sep. 9, 2004

(30) Foreign Application Priority Data
Mar. 6, 2003  (JP)  ............... 2003-059345

(51) Int. Cl.
*A61B 5/00* (2006.01)
*A61B 5/02* (2006.01)
(52) U.S. Cl. .................... 600/556; 600/504
(58) Field of Classification Search ........... 600/362, 600/556
See application file for complete search history.

(56) References Cited

U.S. PATENT DOCUMENTS

| | | | |
|---|---|---|---|
| 4,423,736 A | * | 1/1984 | DeWitt et al. ............... 600/306 |
| 4,862,894 A | | 9/1989 | Fujii |
| 4,966,159 A | * | 10/1990 | Maganias ................... 600/556 |
| 6,629,932 B2 | * | 10/2003 | Weber et al. ............... 600/529 |
| 6,862,542 B2 | * | 3/2005 | Lockhart et al. ............ 702/76 |

* cited by examiner

*Primary Examiner*—Max F. Hindenburg
*Assistant Examiner*—H. Q. Nguyen
(74) *Attorney, Agent, or Firm*—Frishauf, Holtz, Goodman & Chick, P.C.

(57) ABSTRACT

An apparatus for inspecting an allergic reaction projects laser light onto an object having a bloodstreams and receives, using a light sensor, light rays scattered by blood cells at the surface of the object. Based on signals output from the light sensor, the apparatus calculates respective relative values of the bloodstreams at a portion of the object subjected to an allergic reaction test, wherein the relative values are relative to an average value of the bloodstreams measured at a portion of the object other than the portion subjected to the allergic reaction test which is not affected by the allergic reaction test. The apparatus displays the obtained relative values.

2 Claims, 3 Drawing Sheets

APPARATUS FOR INSPECTING ALLERGIC REACTION

BACKGROUND OF THE INVENTION

1. Field of the Invention

The present invention relates to an apparatus for inspecting an allergic reaction which is to show a degree of the reaction, particularly in a patch test for checking the presence or absence of a skin allergic reaction before treatment or surgery, etc., to an apparatus which can show the degree of the reaction with a numerical value.

2. Prior Art

There are some cases to cause an allergic reaction to skin by a substance which usually contacts with the skin such as cosmetics, fibers, metals, etc., and itching or inflammation sometimes remains on the skin. These reactions vary depending on individuals and can be generally expected by an inspection so-called a patch test. This test is carried out by adhering to skin a patch in which a solution which causes a certain allergic reaction with the skin is soaked at a fiber layer placed at the center portion of a thin adhesive sheet, peeling the patch after 1 or 2 days from adhesion and evaluating the presence or absence of, or the degree of flare with naked eyes.

The above judging method has now been widely spread but the judgment is carried out with naked eyes, so that the judgment is fluctuated by individuals and is a less objectivity. Also, in colored peoples, judgment becomes difficult as a density of melanin dye contained in the skin becomes high. Accordingly, it has been demanded to develop any quantitative measurement means with regard to the degree of flare, but at present, any effective means has neither been proposed nor practically been developed.

Generally speaking, flare or itching designates that an inflammation occurs at the portion and it can be considered to be a high bloodstream rate at the portion. Accordingly, if a means to measure how much is a bloodstream rate at the center portion of the flare portion higher than a peripheral portion of the flare portion is found out, it can be realized to quantification of a skin allergic reaction.

There are various means to measure a skin bloodstream, and the most frequently used is a method of using a laser Doppler blood-flowmetry. This method is carried out by preparing a pair of optical fibers, and laser light is irradiated to skin from one of the optical fibers. Then, reflected and scattered light is received by the other optical fiber to measure a Doppler shift frequency generated by movement of blood cells. In this method, however, a bloodstream value at one point alone can be measured, so that to measure the state of the patient, it is necessary to carry out the measurement of the bloodstream at several points by moving the probe and an average value thereof is to be calculated. Moreover, it is difficult to properly evaluate an increased percentage of the bloodstream.

The inventor has invented a monitoring system of a bloodstream distribution called "laser speckle flowgraphy" (hereinafter abbreviated to as "LSFG") due to image analyses of laser scattered light in U.S. Pat. No. 4,862,894 whole contents of which are incorporated herein by reference, which relates to an apparatus for monitoring a bloodstream and put into practice in the field of ophthalmology. This method is to irradiate broadened laser beam to living tissue such as the retina and skin, detect a granular pattern (which is laser speckle) with an image sensor placed on an image plane, and then, display the results as a map state by calculating a rate of time variation of speckles at the respective image elements. According to this system, bloodstream map for a wide area of the surface layer of a living body can be shown as an image with a measurement.

It is possible to carry out an evaluation of the patch test using the LSFG apparatus, but there are some problems. First, in the LSFG system, bloodstream values measured are values shown only by an arbitrary unit having no dimension. Thus, a user usually wishes to know actual values (mm/sec) of the bloodstream velocity at the measured portion and likely say a complaint about the fact that the actual values are unknown.

In an actual LSFG apparatus presently used, there is neither function to obtain a value of bloodstream as a ratio based on a certain point as a standard nor function to show the results as a two-dimensional map or a graph.

There is also no function in the actual LSFG apparatus presently used to obtain an increased value of bloodstream at a tested portion by a patch test in a percentage relative to the portion other than the tested portion, and to display the results with single numerical value.

Moreover, when an allergen of a person to be tested is to be specified among a material which contains a large number of components such as a cosmetic, etc., it cannot help estimating the allergen(s) from the data of the patch test with naked eyes. However, it is extremely difficult to estimate the degree of the allergic reaction with higher precision by the above-mentioned evaluation method of several degrees such as +, ++, etc. Thus, one wishes to develop a sole use system for the patch test, there are some points to be improved in the actually using LSFG system.

In the actual patch test, a circular fiber layer into which a solution to be tested is impregnated is adhered to a skin of a person to be tested, peeled off after lapse of a certain period of time and judged whether flare appears or not at the portion of the patch to which the test solution is impregnated with naked eyes. In such a case, it is a main object to investigate whether the bloodstream at the flare portion is increased with a certain degree as compared to the peripheral portions, and absolute values of the bloodstream rates are not considered. Only when the bloodstream values at the peripheral portion of the portion to be tested are measured as a standard, and relative values at the respective points based on the standard value are obtained and shown in a map state, required information can be obtained.

Moreover, by obtaining simple numerical values in which whether how many percentages the average bloodstream values at the circular region at which the patch test is carried out and the allergic reaction occurred are increased as compared to those at the peripheral portion, objective data substitute for judgment with naked eyes can be provided, so that it can be avoided to make a wrong diagnosis, etc.

According to judgment with naked eyes, if it is a two-step evaluation such as + and ++, it can be easily judged, but if it is an intermediate value, only a person skilled in the art can be judged. As compared with this judgment, by a method of detecting the bloodstream with a degree of percentages, precision with two-digit can be easily obtained and the test results of the bloodstreams can be obtained by the same numerical values irrespective of a person to be inspected. Moreover, a slight change whether how many percentages the portion to be inspected are increased as compared to the data measured yesterday can be easily checked when the previous data measured before is input in a computer.

Furthermore, if a color of the skin of a person to whom the patch test for checking an allergen(s) is carried out is dark or black, the results of the patch test can be hardly judged with naked eyes. However, when the measured bloodstream values at the portion in which the patch test had been carried out can be shown with numerical values, the results of the patch test can be easily obtained irrespective of the color of the skin and the allergen(s) can be easily specified.

SUMMARY OF THE INVENTION

An object of the present invention is to provide an apparatus for inspecting an allergic reaction which can show a degree of a reaction, particularly, in a patch test for checking the presence or absence of a skin allergic reaction before treatment or surgery, etc., to an apparatus which can show the degree of the reaction with a numerical value.

The present invention relates to an apparatus for inspecting an allergic reaction comprising
 a light-projecting means for projecting a laser light upon an object having a bloodstream;
 a light-receiving means for receiving a plurality of laser beams scattered by blood cells at the plurality of points on a surface of the object;
 a memory means for storing output signals read out of the light receiving elements;
 a calculating means for calculating from the output signals stored in the memory means to derive information about the bloodstream; and
 a display means for displaying the information in a map state,
 wherein the calculating means comprises calculating relative values of the respective bloodstreams at measured portions to be tested the allergic reaction or subjected to a patch test based on an average value of a bloodstream measured at portions other than the portion to be tested or subjected to the patch test and not affected by the patch test as a standard value, and
 the display means comprises plotting the relative values obtained by the calculating means.

The present invention also relates to a method of inspecting an allergic reaction of a skin after subjected to a patch test for checking an allergen(s), which comprises the steps of:
 projecting a laser light upon an object having a bloodstream subjected to the path test by a light-projecting means;
 receiving a plurality of laser beams scattered by blood cells at the plurality of points on a surface of the object subjected to the patch test by a light-receiving means;
 storing output signals read out of the light receiving elements by a memory means;
 calculating from the output signals stored in the memory means to derive information about the bloodstream by a calculating means; and
 displaying the information in a map state by a display means;
 wherein relative values of the respective bloodstreams at measured portions to be tested the allergic reaction or subjected to a patch test are calculated by the calculating means based on an average value of a bloodstream measured at portions of the skin other than the portion subjected to the patch test and not affected by the patch test as a standard value, and
 the relative values obtained by the calculating means are plotted by the display means as a two- or three-dimensional map.

DESCRIPTION OF THE PREFERRED EMBODIMENTS

Figure 1:
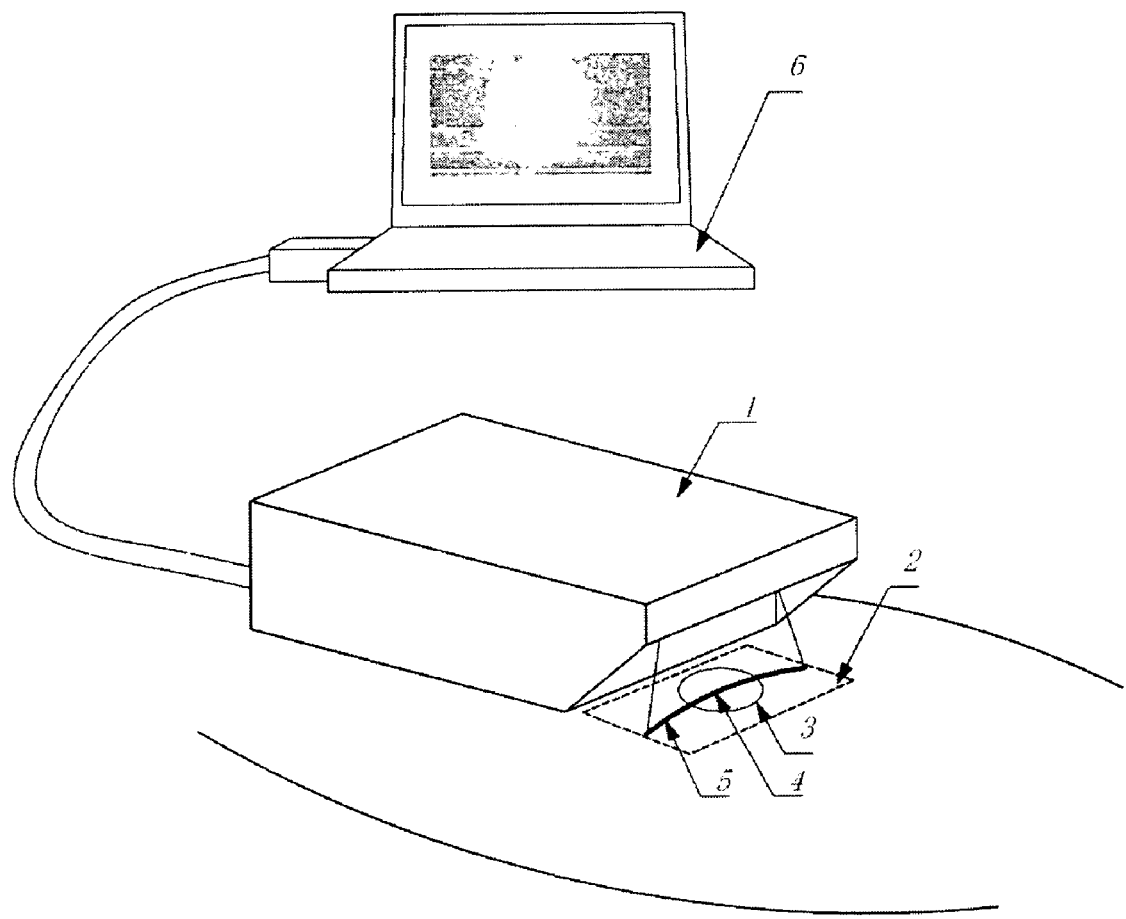
FIG. 1 is a perspective view showing a measurement of the present invention to measure a bloodstream at a flare portion by a patch test by placing a probe on a skin.

In the preferred embodiments of the present invention, the display means preferably displays the relative values of the bloodstream with different color codes or gray scales in a two- or three-dimensional map, or it displays linearly extracted data along a specific direction in a line chart. Here, the relative value means a value obtained by dividing respective measured values of the bloodstreams inspected at the measured region by an average value of the bloodstream obtained at a region which does not subject to a patch test.

In the apparatus of the present invention, the calculating means preferably has a memory in which a standard value of the bloodstream measured at a portion sufficiently apart from a portion to be inspected or measured at the same portion as the portion to be inspected before the test is carried out is stored, and has a function of calculating the relative value of the bloodstream at the portion subjected to the test based on the standard value. For example, when a patch test is carried out by adhering the patch to the left hand of a person, an average value of the bloodstream at the right hand of the person can be used as a standard value. Or else, before subjecting to the patch test, an average value of the bloodstream of a person to be inspected is previously measured, and then, measured values after subjecting to the patch test are divided by the average value to obtain relative values at the respective measured portions.

The calculating means also preferably has a function that can calculate an average bloodstream value $Av_1$ at the portion to be inspected or subjected to a patch test for inspecting an allergic reaction(s) and convert the average bloodstream value $Av_1$ to a relative value $Av_2$ by dividing the above value $Av_1$ by an average bloodstream value $Av_3$ measured at a portion other than the portion to be inspected or subjected to the patch test, i.e., $Av_2=Av_1/Av_3$.

The calculating means further preferably has a function that can obtain an average bloodstream value $Av_3$ measured at portions other than the portion to be inspected or subjected to the patch test, can take in measured values $V_n$ at the portion to be inspected or subjected to a patch test for inspecting an allergic reaction(s), can calculate a new map of bloodstream with relative values $R_n$ by dividing the measured values $V_n$ by the average bloodstream value $Av_3$ and can calculate an average value $Av_4$ by averaging over the values ($R_n$) within the portion to be inspected or subjected to the patch test. That is, an average bloodstream value $Av_3$ at the portions other than the portion subjected to the patch test is firstly obtained and then, the respective values $V_n$ measured at the portion subjected to the patch test are obtained, then, relative values $R_n$ at the respective portions subjected to the patch test are obtained by dividing the measured values $V_n$ by the average bloodstream value $Av_3$, and an average value $Av_4$ which is an average value of the $R_n$ is obtained.

The calculating means further preferably has a function that can calculate an average bloodstream value $Bv_1$ at the portion to be inspected or subjected to a patch test for inspecting an allergic reaction(s) by the laser, identify a region at which a bloodstream value is higher than the average value $Bv_1$, calculate an average bloodstream value $Bv_2$ at the region at which a bloodstream value is higher than the average value $Bv_1$, calculate an average bloodstream value $Bv_3$ at a region other than the region at which a bloodstream value is higher than the average value $Bv_1$, and divide the average bloodstream value $Bv_2$ by the average bloodstream value $Bv_3$. That is, a region showing higher bloodstream values are automatically identified by the apparatus, and the average values $Bv_1$, $Bv_2$ and $Bv_3$ are calculated and the ratios of $Bv_2/Bv_3$ at the respective points inspected are calculated.

Figure 4:
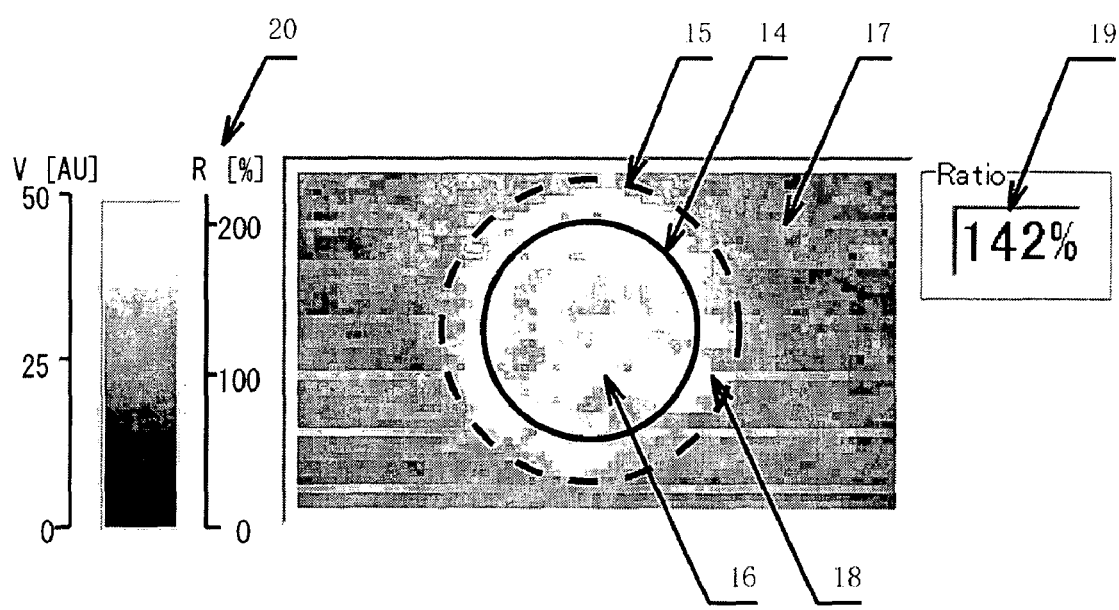
FIG. 4 is a map converting the raw data shown in FIG. 3 into relative values by the apparatus of the present invention.

The calculating means further preferably has a function that can calculate an average bloodstream value $Bv_4$ which corresponds to the reference numeral 17 of FIG. 4 measured at a portion other than a portion to be inspected or subjected to a patch test for inspecting an allergic reaction(s) and calculate an average bloodstream value $Bv_1$ which corresponds to the reference numeral 16 of FIG. 4 at the portion to be inspected or subjected to a patch test for inspecting an allergic reaction(s) both of the average values $Bv_1$ and $Bv_4$ excludes the value measured at a portion 18 of FIG. 4 peripheral to the portion 16 of FIG. 4 to be inspected or subjected to the patch test, and divide the average bloodstream value $Bv_1$ by the average bloodstream value $Bv_4$ as a standard value. That is, at the portion 18 peripheral to the portion to be inspected or subjected to the patch test, bloodstream value tends to show higher than the portion far from the portion 17 to be inspected or subjected to the patch test. Thus, a relative value of the bloodstream at the portion 16 to be inspected or subjected to the patch test is obtained from the ratios of $Bv_1/Bv_4$ at the respective points inspected excluding or leaving from the value measured at the portion 18 peripheral to the portion 16 to be inspected or subjected to the patch test.

The display means of the present invention preferably has a function that can display change in bloodstream at the portion to be inspected with relative values with a lapse of time or that can set a time at which a factor which changes the bloodstream occur, and a function that can display the difference between the above time and the present time.

The display means further preferably has a function that can display past measurement history of an allergic reaction(s) based on factors which cause change in bloodstream such as allergen(s) with regard to respective specimen to be inspected.

In the present invention, the apparatus is an apparatus in which the calculating means preferably calculates correlation of the relative value of the bloodstream at the portion to be inspected and an amount of stimulus causing the change in bloodstream, and identifies a stimulus, or a combination of stimuli having the highest correlation as a cause for changing the bloodstream value.

In the method of monitoring bloodstreams of a skin after subjected to a patch test for checking an allergen(s), the same as mentioned above can be applied to.

In the following, the present invention will be explained in more detail by referring to the drawings.

EXAMPLES

The present invention is explained by referring to a small sized measurement probe shown in FIG. 1 as an example. In FIG. 1, the reference numeral 1 is a measurement probe body. 2 is a surface to be inspected such as a skin at an upper portion, 3 is a flare dot generated by a patch test, 4 is a linear laser spot, 5 is a peripheral portion of the spot, and 6 is a space cut the probe so that the portion to be inspected can be observed from a slightly upper portion (a laptop computer to display the map of bloodstream). The position of the probe is, for example, firstly set so as to scan the center portion of the flare dot 3 by the linear laser spot, and then, the measurement is carried out.

Figure 2:
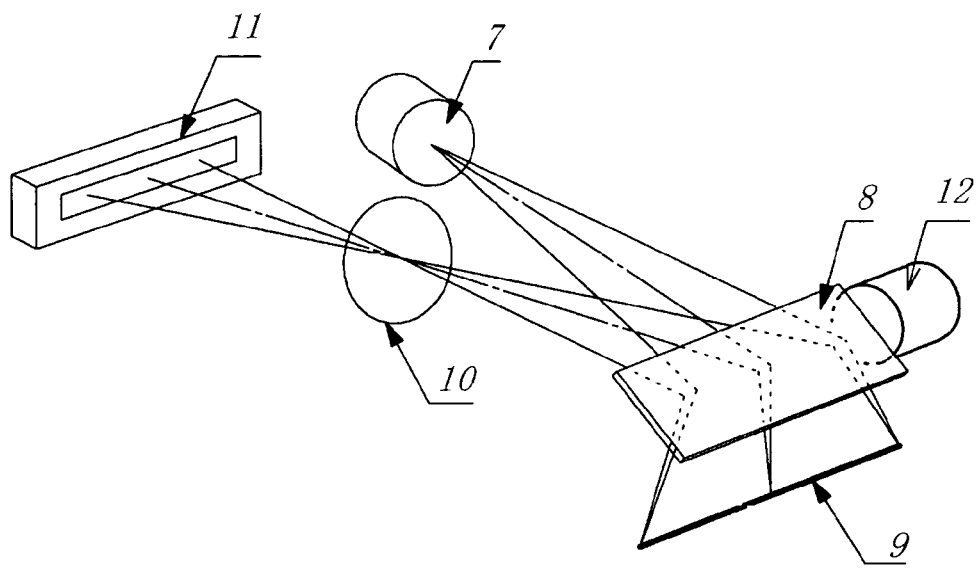
FIG. 2 is a perspective view showing an example of constitution of an optical system at the inside of the probe of the present invention.

FIG. 2 shows a perspective view illustrating one embodiment of the apparatus of the present invention and shows a constitution at the inside of the probe. In FIG. 2, light emitted from a light source portion 7 which are so designed that a beam is emitted to a linear state by attaching a cylindrical lens to an end portion of emission of a laser such as a semiconductor laser, a He—Ne laser, etc., is bent substantially a right angle by a reflection mirror 8 to project a linear laser spot 9 on the surface of a skin. The laser light scattered by a linear laser spot 9 forms an image speckle on a line sensor 11 through a lens 10.

A signal detected at the line sensor 11 is recorded to a memory of a microcomputer in the probe, and bloodstream values based on a time change ratio of the speckle are obtained with regard to the respective points on the line (state) spots. Next, the reflection mirror 8 is rotated by a motor 12, and calculation is repeated to obtain a two-dimensional bloodstream map, which can be carried out in the same manner as mentioned in U.S. Pat. No. 4,862,894. If a significant allergic reaction occurred, the bloodstream value at the center portion of the map is increased. When scanning is carried out continuously or discontinuously for a certain surface area of the skin with several portions to be inspected, and then, the measured values are calculated by a microcomputer, it is possible to show the results of the relative values of bloodstreams at the measured respective points or change in the relative values of bloodstreams with a lapse of time by a three-dimensional bloodstream map.

Figure 3:
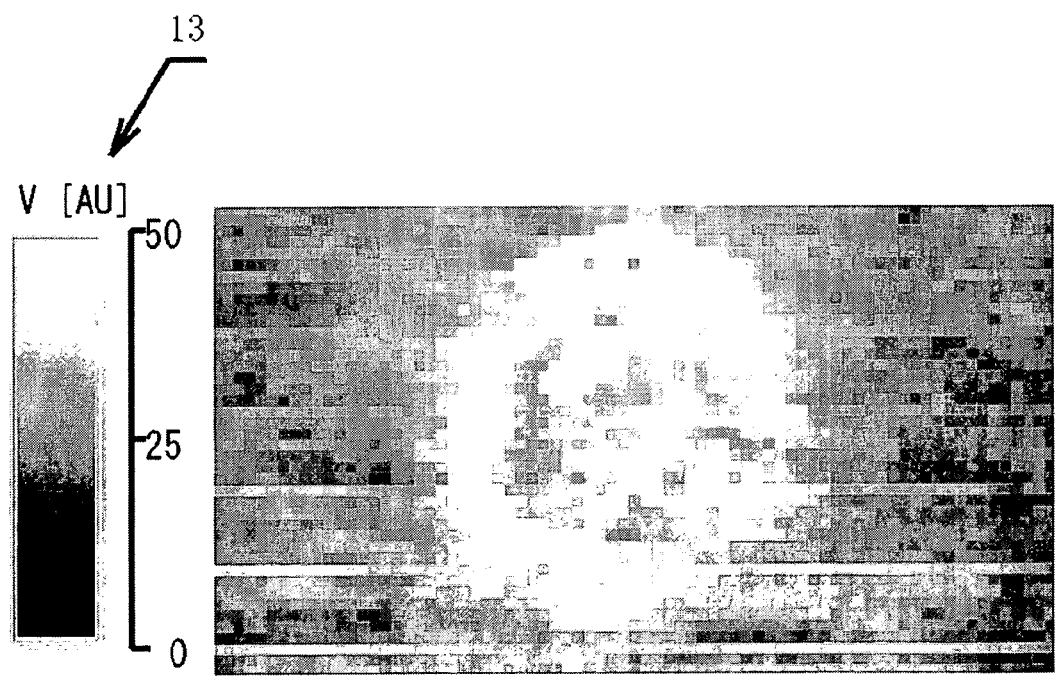
FIG. 3 is a map showing an example of measured raw data of the bloodstream distribution obtained by the present apparatus, which shows that the bloodstream is enhanced in the central circular area where one allergic reaction occurs.

FIG. 3 is a map showing an example of measured raw data which are measured values $V_n$ of bloodstreams at the portions subjected to a patch test for inspecting an allergic reaction and around the portions thereof using an apparatus of the present invention and shown in a map state utilizing a graphic function of a personal computer before converting the raw data into relative numerical values. Here, the reference numeral 13 shows a color code of the measured raw values $V_n$ with an arbitrary unit (AU). In a conventional LSFG apparatus, it can be observed that a bloodstream rate becomes high only at a center circular region. However, in the apparatus of the present invention, by pointing a cursor of a personal computer to a center portion of the measured values and click it, two circular regions 16 and 18 are set as shown in FIG. 4.

That is, in FIG. 4, an inner circle 14 is a circle corresponding to a size of a patch tested for an allergic reaction and an inside region 16 of the circle 14 is defined to be a region at which an allergic reaction had occurred. In an actual test, the allergic reaction spreads on the skin broader than the above circle 14 to a region 10 to 20% broader than the circle, so that an accurate evaluation cannot be done otherwise excluding values deducing the values between a circle 15 and the circle 14, i.e., the region 18, and a region 17 outside the circle 15 is used as a standard value for comparing the bloodstream values. In FIG. 4, the reference numeral 19 is a value showing the result of a relative value (percentage) of the bloodstream at the region 16 and the reference numeral 20 is a color code of the measured raw values $V_n$ (V) with an arbitrary unit (AU) and the relative values $R_n$ (R) with a percentage (%). A new index to show the allergic reaction quantitatively can be obtained by two methods. One of which is to obtain an average value of a bloodstream with regard to the region of 16 and 17 shown in FIG. 4, and a relative value obtained by dividing ale former value by the latter value can be shown with relative values or percentages. The other is to obtain an average value of the bloodstream at the region 17, and the respective bloodstream values in the map is divided by the average value to obtain a relative value or percentage and to show these values to a map. When an average value measured at the region 16 after conversion on the map is calculated, the results become an index of the allergic reaction, which coincide with the numerical values obtained by the first method. The results can be shown as the reference numeral 19 shown in FIG. 4 as, for example, "142%".

When the allergic reaction is spread to a wide range, the values show higher value within the whole range to be observed, so that a means in which bloodstream values sufficiently far from the portion showing the allergic reaction are measured and the average value at the portion is input as a standard value whereby an increased ratio of the bloodstream is calculated thereon may be provided.

The patch test is extremely effective for judgment of an allergic reaction of a skin, but the reaction was judged with naked eyes of a judge, so that the results are determined by the subjectivity of the judge and strict comparison is also difficult. In the present invention, increase in bloodstream due to inflammation can be precisely measured and the inflammation can be correctly expressed with a numerical value as an increased ratio of the bloodstream. Thus, it is possible to carry out quantitative evaluation of the patch test. In particular, when a density of melanin dye contained in the skin is extremely high, it was almost impossible to judge flare with naked eyes. In such a case, increase in the bloodstream values can be precisely measured and easily judged.

Moreover, when an allergen(s) is/are to be identified in a composition containing various kinds of components such as cosmetics, etc., it is necessary to obtain precise data of the allergic reactions of the respective components. According to the apparatus and the method of present invention, the allergic reaction can be evaluated with a two-digit precision. Accordingly, when a calculating means for obtaining a correlation coefficient between the obtained results, i.e., measured values, and a contained amount of the respective components in a specimen solution used for the measurement is provided to the apparatus of the present invention, the allergen(s) can be specified with a small number of inspection and high precision.

The invention claimed is:

1. An apparatus for inspecting an allergic reaction comprising:
    light-projecting means for projecting a laser light onto an object having a plurality of bloodstreams and into an area including a portion subjected to an allergic reaction test;
    light-receiving means for receiving light rays scattered by blood cells at a plurality of points at a surface of the object;
    memory means for storing output signals from the light-receiving means;
    calculating means for calculating, based on the output signals stored in the memory means, respective relative values of the bloodstreams at the portion of the object subjected to the allergic reaction test, said relative values being relative to an average value of the bloodstreams measured at a portion of the object other than the portion subjected to the allergic reaction test which is not affected by the allergic reaction test; and
    display means for displaying the relative values obtained by the calculating means;
    wherein the calculating means is arranged to:
        calculate an average bloodstream value $Bv_1$ of the entire area of the object onto which the laser light is projected;
        identify a region, of the area of the object onto which the laser light is projected, at which a bloodstream value is higher than the average bloodstream value $Bv_1$;
        calculate an average bloodstream value $Bv_2$ measured at the identified region at which the bloodstream value is higher than the average value $Bv_1$;
        calculate an average bloodstream value $Bv_3$ measured at a region, of the area of the object onto which the laser light is projected, other than the region at which a bloodstream value is higher than the average value $Bv_1$; and
        divide the average bloodstream value $Bv_2$ by the average bloodstream value $Bv_3$ to calculate a degree of the allergic reaction;
    wherein the display means is arranged to further display the calculated degree of the allergic reaction at least as a numerical value; and
    wherein the allergic reaction test is a patch test.

2. A method of inspecting an allergic reaction comprising:
    projecting a laser light onto an object having a plurality of bloodstreams and into an area including a portion subjected to an allergic reaction test;
    receiving, by a light sensor, light rays scattered by blood cells at a plurality of points at a surface of the object;
    storing output signals from the light sensor;
    calculating, based on the stored output signals, respective relative values of the bloodstreams at the portion of the object subjected to the allergic reaction test, said relative values being relative to an average value of the bloodstreams measured at a portion of the object other than the portion subjected to the allergic reaction test which is not affected by the allergic reaction test; and
    displaying the calculated relative values;
    wherein the calculating comprises:
        calculating an average bloodstream value $Bv_1$ at the entire area of the object onto which laser light is projected;
        identifying a region, of the area of the object onto which laser light is projected, at which a bloodstream value is higher than the average bloodstream value $Bv_1$;
        calculating an average bloodstream value $Bv_2$ measured at the region at which the bloodstream value is higher than the average value $Bv_1$;
        calculating an average bloodstream value $Bv_3$ measured at a region, of the area of the object onto which laser light is projected, other than the region at which a bloodstream value is higher than the average value $Bv_1$; and
        dividing the average bloodstream value $Bv_2$ by the average bloodstream value $Bv_3$ to calculate a degree of the allergic reaction;
    wherein the displaying comprises displaying the degree of the allergic reaction at least as a numerical value; and
    wherein the allergic reaction test is a patch test.

* * * * *